United States Patent

Abou-Gharbia

Patent Number: 4,754,038
Date of Patent: Jun. 28, 1988

[54] CARBOLINE HISTAMINE $H_1$ ANTAGONISTS

[75] Inventor: Magid A. Abou-Gharbia, Wilmington, Del.

[73] Assignee: American Home Products Corporation, New York, N.Y.

[21] Appl. No.: 19,087

[22] Filed: Feb. 26, 1987

[51] Int. Cl.⁴ .......................................... C07D 471/04
[52] U.S. Cl. ...................................... 546/87; 546/85; 546/86
[58] Field of Search ............................ 546/85, 86, 87

[56] References Cited

U.S. PATENT DOCUMENTS 3,502,688  3/1970  Berger et al. ..................... 546/87
3,522,262  7/1970  Berger et al. ..................... 546/87

OTHER PUBLICATIONS

Herbert et al., J. Med. Chem. 23, 635 (1980).
Derwent Abstract 31,954 (U.S. Pat. No. 3,382,250).
Derwent Abstract 08747 (J5 5154-972).

*Primary Examiner*—Mary C. Lee
*Assistant Examiner*—J. Richter
*Attorney, Agent, or Firm*—Richard K. Jackson

[57] ABSTRACT

Histaminic $H_1$-receptor antagonists of the formula:

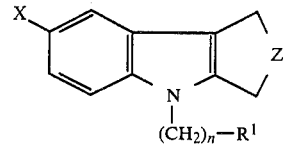

in which
$R^1$ is

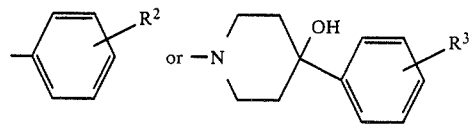

where $R^2$ is hydrogen, alkyl of 1 to 3 carbon atoms, alkoxy of 1 to 3 carbon atoms, halo, nitro, cyano or trifluoromethyl; and $R^3$ is hydrogen, alkyl of 1 to 3 carbon atoms, alkoxy of 1 to 3 carbon atoms, halo, nitro, cyano or trifluoromethyl;
X is hydrogen, alkyl of 1 to 3 carbon atoms, alkoxy of 1 to 3 carbon atoms or halo;
Z is

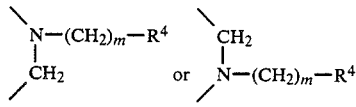

where $R^4$ is pyridinyl, quinolinyl or benzoyl, any of which may be substituted by alkyl of 1 to 4 carbon atoms, alkoxy of 1 to 3 carbon atoms, halo or trifluoromethyl; and m is one of the integers 2, 3 or 4; and
n is one of the integers 1, 2, 3 or 4;
or a pharmaceutically acceptable salt thereof.

8 Claims, No Drawings

CARBOLINE HISTAMINE H₁ ANTAGONISTS

BACKGROUND OF THE INVENTION

Harbert et al., J. Med. Chem. 23 635 (1980) disclose a group of 5-aryltetrahydrogamma-carboline derivatives which posses neuroleptic activity.

DESCRIPTION OF THE INVENTION

In accordance with this invention there is provided a group of histamine H₁-antagonists of the formula:

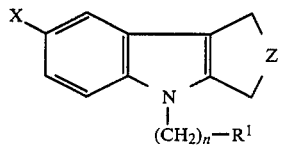

in which
R¹ is

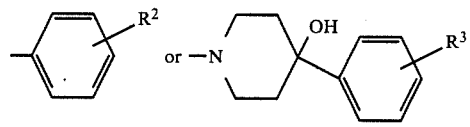

where R² is hydrogen, alkyl of 1 to 3 carbon atoms, alkoxy of 1 to 3 carbon atoms, halo, nitro, cyano or trifluoromethyl; and R³ is hydrogen, alkyl of 1 to 3 carbon atoms, alkoxy of 1 to 3 carbon atoms, halo, nitro, cyano or trifluoromethyl;

X is hydrogen, alkyl of 1 to 3 carbon atoms, alkoxy of 1 to 3 carbon atoms or halo;

Z is

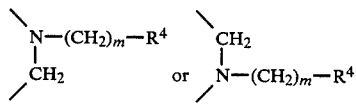

where R⁴ is pyridinyl, quinolinyl or benzoyl, any of which may be substituted by alkyl of 1 to 4 carbon atoms, alkoxy of 1 to 3 carbon atoms, halo or trifluoromethyl; and m is one of the integers 2, 3 or 4; and n is one of the integers 1, 2, 3 or 4;

or a pharmaceutically acceptable salt thereof.

The beta-carboline derivatives of this group present compounds of the formula:

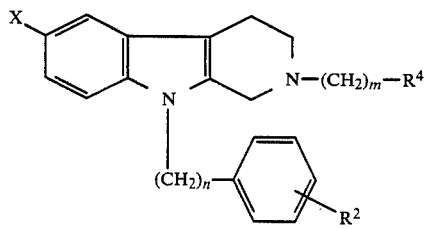

in which

R² is hydrogen, alkyl of 1 to 3 carbon atoms, alkoxy of 1 to 3 carbon atoms, halo, nitro, cyano or trifluoromethyl;

n is one of the integers 1, 2, 3 or 4;

R⁴ is pyridinyl, quinolinyl or benzoyl, any one of which may be substituted by alkyl of 1 to 4 carbon atoms, alkoxy of 1 to 3 carbon atoms, halo or trifluoromethyl;

m is one of the integers 2, 3 or 4; and

X is hydrogen, alkyl of 1 to 3 carbon atoms, alkoxy of 1 to 3 carbon atoms, or halo;

or a pharmaceutically acceptable salt thereof.

The gamma-carboline derivatives of this invention present the structural formula:

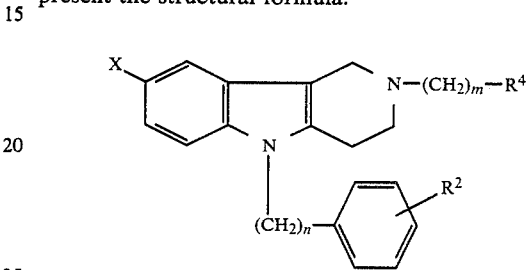

in which

R² is hydrogen, alkyl of 1 to 3 carbon atoms, alkoxy of 1 to 3 carbon atoms, halo, nitro, cyano or trifluoromethyl;

n is one of the integers 1, 2, 3 or 4;

R⁴ is pyridinyl, quinolinyl or benzoyl, any one of which may be substituted by alkyl of 1 to 4 carbon atoms, alkoxy of 1 to 3 carbon atoms, halo or trifluoromethyl;

m is one of the integers 2, 3 or 4; and

X is hydrogen, alkyl of 1 to 3 carbon atoms, alkoxy of 1 to 3 carbon atoms, or halo;

or a pharmaceutically acceptable salt thereof.

In the compounds depicted above, the preferred pyridinyl and quinolinyl moieties representing R⁴ are 2-pyridinyl, 3-pyridinyl, 4-pyridinyl, 2-quinolinyl and 4-quinolinyl with 2-pyridinyl being most preferred. The preferred benzoyl moiety is 4-tert-butylbenzoyl. The preferred group representing R¹ is the phenyl and 4-halophenyl moieties where halo represents —Cl, —Br or F, with fluoro being the most preferred halo substituent. The preferred group representing X is halo, more specifically —Cl, —Br, or —F, with fluorine being the most preferred halogen.

The pharmaceutically acceptable salts of the histamine H₁ antagonists of this invention are prepared by conventional means and are derived with either inorganic or organic acids such as hydrochloric, hydrobromic, sulfuric, phosphoric, nitric, acetic, fumaric, citric, tartaric, maleic, lactic, 2-hydroxyethanesulfonic, methanesulfonic, toluene-4-sulfonic, ethanesulfonic acid, and the like.

The compounds of this invention are preparable by a variety of synthetic routes using conventional methods. Thus, the appropriately substituted beta-carboline [Mioque et al., Compt. Rend. 252 2416 (1961)] or gamma-carboline [Harbert et al., J. Med. Chem. 23 635 (1980)] are N-alkylated on the carboline nitrogen atom with Halo—(CH₂)ₘ—R⁴ where Halo is —Cl or —Br, in dimethylformamide in the presence of an acid receptor such as Na₂CO₃ or Cs₂CO₃; or with CH₂=CH—R⁴ in the presence of glacial acetic acid. The product is N- alkylated at the indolic nitrogen atom with Halo—$(CH_2)_n$—$R^1$ in dimethylformamide in the presence of a strong base such as sodium hydride or n-butyl lithium.

The following examples illustrate the preparation of representative compounds of the invention.

EXAMPLE 1

2,3,4,9-Tetrahydro-9-(phenylmethyl)-2-[2-(2-pyridinyl)ethyl]-1H-pyrido[3,4-b]indole A mixture of 2,3,4,9-tetrahydro-1H-pyrido[3,4-b]indole (1.72 g., 0.01 mol), 2-vinylpyridine (1.0 g., 0.01 mol) and 2 ml. of glacial acetic acid were refluxed in 25 ml. of methanol for 24 hours. The solvent was removed in vacuo and the separated solid was suspended in water. The solution was made slightly basic via the addition of solid potassium carbonate and it was extracted with methylene chloride (4×150 ml.). The methylene chloride layer was dried over anhydrous sodium sulfate and evaporated under reduced pressure to afford 1.2 g. (44% yield) of 2,3,4,9-tetrahydro-2-[2-(2-pyridinyl)ethyl]-1H-pyrido[3,4-b]indole. This intermediate was dissolved in 50 ml. of dimethylformamide and 0.92 g. (0.04 mol) of sodium hydride was added and stirring was continued for 1 hour. To the stirred solution 0.66 g. (0.004 mol) of benzyl bromide was added and the reaction mixture was stirred at room temperature overnight. The solvent was removed under vacuum and the solid residue was suspended in water and extracted with methylene chloride (3×100 ml.). The organic layer was separated, dried and evaporated. The remaining oil was dissolved in ethanol and converted to the dihydrochloride salt; mp 278°–280° C.

Analysis for: $C_{25}H_{25}N_3.2HCl$: Calculated: C, 68.18; H, 6.13; N, 9.54; Found: C, 68.05; H, 6.34; N, 9.51.

EXAMPLE 2

9-[(4-fluorophenyl)methyl]-2,3,4,9-tetrahydro-2-[2-(2-pyridinyl)ethyl]-1H-pyrido[3,4-b]indole The title compound was prepared following procedure of Example 1 with the exception that 4-fluorobenzyl bromide was used instead of benzyl bromide. The product was converted to the hydrochloride salt, quarter hydrate; mp. 208°–210° C.

Analysis for: $C_{25}H_{24}FN_3.2HCl.1/4H_2O$: Calculated: C, 64.86; H, 5.73; N, 9.08; Found: C, 64.88; H, 5.79; N, 9.03.

EXAMPLE 3

1-[4-(1,1-dimethylethyl)phenyl]-4-[9-[(4-fluorophenyl)methyl]-1,3,4,9-tetrahydro-2H-pyrido[3,4-b]indole-2yl]-1-butanone The title compound was prepared following procedure of Example 1 with the exception that 4-(1,1-dimethylethyl)phenyl-ω-chlorobutyrophenone was used instead of 1,3-dibromopropane to afford 1-[4-(1,1-dimethylethyl)phenyl]1,3,4,9-tetrahydro-2H-pyrido[3,4-b]indole as an intermediate.

The title compound was prepared by reacting this intermediate with 4-fluorobenzyl bromide following procedure of Example 1 and the product was converted to the fumarate salt; mp 200°–202° C.

Analysis for: $C_{32}H_{35}FN_2O.C_4H_4O_4$: Calculated: C, 72.24; H, 6.52; N, 4.68; Found: C, 72.65; H, 6.67; N, 4.95.

EXAMPLE 4

8-Fluoro-5-[(4-fluorophenylmethyl)]-2,3,4,5-tetrahydro-2-[2-(2-pyridinyl)ethyl]-1H-pyrido[4,3-b]indole, dihydrochloride The title compound was prepared following procedure of Example 1 with the exception 8-fluoro2,3,4,5-tetrahydro-1H-pyrido[4,3-b]indole was used instead of 2,3,4,9-tetrahydro-1H-pyrido[3,4-b]indole and 4-fluorobenzyl bromide instead of benzyl bromide and was converted to the hydrochloride salt; mp 257°–260° C.

Analysis for: $C_{25}H_{23}F_2N_3.2HCl$: Calculated: C, 63.02; H, 5.25; N, 8.82; Cl, 14.91; Found: C, 62.50; H, 5.34; N, 8.62; Cl, 14.63.

EXAMPLE 5

4-(4-chlorophenyl)-1-[3-[1,2,3,4-tetrahydro-2-[2-(2-pyridinyl)ethyl]9H pyrido[3,4-b]indole-9-yl]propyl]-4-piperidinol The title compound was prepared following procedure of Example 1 with the exception that 1-[bromopropyl-4-(4-chlorophenyl)]-4-piperidinol was used instead of benzyl bromide. The product was converted to the trihydrochloride salt, which was recovered as a trihydrate; mp 150°–153° C.

Analysis for: $C_{32}H_{37}N_4ClO.3HCl.3H_2O$: Calculated: C, 55.49; H, 6.68; N, 8.09; Found: C, 55.34; H, 6.31; N, 7.74.

The compounds of this invention were established to be histamine $H_1$-antagonists by subjecting them to the following standard test procedures for $H_1$-blocking activity:

Fresh segments of terminal ileum immediately proximal to Peyer's patch, obtained from male Buckshire guinea pigs, were suspended in 37° C. Tyrode's solution in a tissue bath and aerated. The tissue segments were placed under one gram tension and allowed to equilibrate for one hour. Histamine was added to each tissue bath to a final concentration of $1\times10^{-6}M$. The contraction response after it equilibrated was noted as grams tension. Test drug was added, in the presence of histamine, to each bath to a final concentration of $1\times10^{-7}M$. The change in grams tension was noted and the percent reduction in grams tension calculated.

Following this procedure, with quadruplicate sets of tissues, the compound of Example 1 demonstrated 59 percent reduction in tissue contraction and the compounds of Example 2, 3, and 4 provided 25, 12, and 29 percent reduction in contraction, respectively.

The pharmacological results obtained characterize the compounds of this invention as $H_1$-receptor antagonists useful in the treatment of mammals experiencing conditions such as asthma, hay fever, allergic rhinitis, atopic dermatitis, conjunctivitis, pruritis, and eczema, or other responses where histamine is released and acts on $H_1$ receptors. As such, they may be administered topically or systemically. Topical administration is advantageously achieved to the skin via creams, ointments or lotions, or via aerosol introduction into the respiratory tract. Systemic administration may be orally or parenterally, including the nasal, introbronchial or rectal routes. In each instance, conventional formulations amenable to use in the desired administration route is appropriate. Hence, tablets and capsules may be prepared for oral administration, suppositories for rectal administration, isotonic aqueous solutions for intravenous, subcutaneous or intramuscular injection and in aerosol suspensions for inhalation.

As is conventional in the use of antihistamine agents, the appropriate dosage is determined on a subjective basis by initial administration of small amounts, ca. 0.5–15 mg. followed by increasing quantities up to about 400 mg., depending upon the desired route of administration, until the desired symptomatic relief is obtained. The dosage is personalized in this manner for each patient, based upon size, age, type of discomfort, degree of disability, etc., by the physician.

What is claimed is:

1. A compound of the formula:

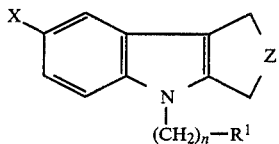

in which $R^1$ is

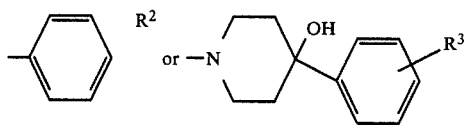

where $R^2$ is hydrogen, alkyl of 1 to 3 carbon atoms, alkoxy of 1 to 3 carbon atoms, halo, nitro, cyano or trifluoromethyl; and $R^3$ is hydrogen, alkyl of 1 to 3 carbon atoms, alkoxy of 1 to 3 carbon atoms, halo, nitro, cyano or trifluoromethyl;

X is hydrogen, alkyl of 1 to 3 carbon atoms, alkoxy of 1 to 3 carbon atoms or halo;

Z is

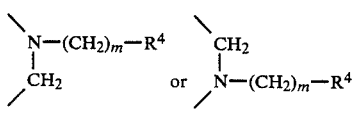

where $R^4$ is pyridinyl, quinolinyl or benzoyl, any of which may be substituted by alkyl of 1 to 4 carbon atoms, alkoxy of 1 to 3 carbon atoms, halo or trifluoromethyl; and m is one of the integers 2, 3 or 4; and n is one of the integers 1, 2, 3 or 4;

or a pharmaceutically acceptable salt thereof.

2. A compound of claim 1 of the formula:

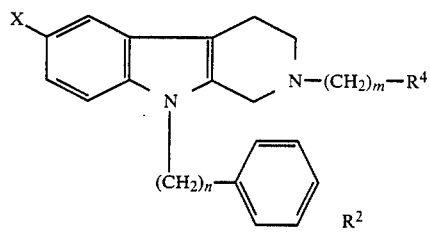

in which $R^2$ is hydrogen, alkyl of 1 to 3 carbon atoms, alkoxy of 1 to 3 carbon atoms, halo, nitro, cyano or trifluoromethyl;

n is one of the integers 1, 2, 3 or 4;

$R^4$ is pyridinyl, quinolinyl or benzoyl, any one of which may be substituted by alkyl of 1 to 4 carbon atoms, alkoxy of 1 to 3 carbon atoms, halo or trifluoromethyl;

m is one of the integers 2, 3 or 4; and

X is hydrogen, alkyl of 1 to 3 carbon atoms, alkoxy of 1 to 3 carbon atoms, or halo;

or a pharmaceutically acceptable salt thereof.

3. A compound of claim 1 of the formula:

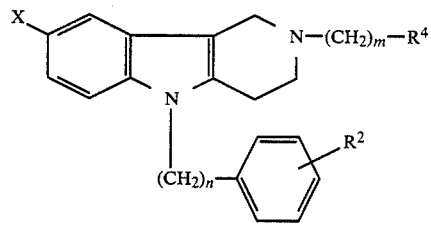

in which $R^2$ is hydrogen, alkyl of 1 to 3 carbon atoms, alkoxy of 1 to 3 carbon atoms, halo, nitro, cyano or trifluoromethyl;

n is one of the integers 1, 2, 3 or 4;

$R^4$ is pyridinyl, quinolinyl or benzoyl, any one of which may be substituted by alkyl of 1 to 4 carbon atoms, alkoxy of 1 to 3 carbon atoms, halo or trifluoromethyl;

m is one of the integers 2, 3 or 4; and

X is hydrogen, alkyl of 1 to 3 carbon atoms, alkoxy of 1 to 3 carbon atoms, or halo;

or a pharmaceutically acceptable salt thereof.

4. The compound of claim 1 which is 2,3,4,9-tetrahydro-9-(phenylmethyl)-2-[2-(2-pyridinyl)ethyl]-1H-pyrido[3,4-b]indole, or a pharmaceutically acceptable salt thereof.

5. The compound of claim 1 which is 9-[(4-fluorophenyl)methyl]-2,3,4,9-tetrahydro-2-[2-(2-pyridinyl)ethyl]-1H-pyrido[3,4-b]indole, or a pharmaceutically acceptable salt thereof.

6. The compound of claim 1 which is 1-[4-(1,1-dimethylethyl)phenyl]-4-[9-[(4-fluorophenyl)methyl]-1,3,4,9-tetrahydro-2H-pyrido[3,4-b]indole-2-yl]-1-butanone, or a pharmaceutically acceptable salt thereof.

7. The compound of claim 1 which is 8-fluoro-5-[(4-fluorophenylmethyl)]-2,3,4,5-tetrahydro-2-[2-(2-pyridinyl)ethyl]-1H-pyrido[4,3-b]indole, or a pharmaceutically acceptable salt thereof.

8. The compound of claim 1 which is 4-(4-chlorophenyl)-1-[1,2,3,4-tetrahydro-2-[2-(2pyridinyl)ethyl]-9H-pyrido[3,4-b]indol-9-yl]propyl]-4-piperidinol, or a pharmaceutically acceptable salt thereof.

* * * * *